United States Patent [19]

Gillings et al.

[11] 4,188,202
[45] Feb. 12, 1980

[54] COMPOSITION

[75] Inventors: Christopher Gillings; Ian C. Jewry, both of Cambridge; Harold G. Haynes, Royston, all of England

[73] Assignee: Fisons Limited, London, England

[21] Appl. No.: 907,848

[22] Filed: May 19, 1978

Related U.S. Application Data

[63] Continuation of Ser. No. 737,987, Nov. 2, 1976, abandoned.

[30] Foreign Application Priority Data

Nov. 12, 1975 [GB] United Kingdom ............... 46659/75

[51] Int. Cl.$^2$ .............................................. A01N 9/00
[52] U.S. Cl. ..................................... 71/88; 71/DIG. 1
[58] Field of Search ............................. 71/88, DIG. 1

[56] References Cited

U.S. PATENT DOCUMENTS

| | | | |
|---|---|---|---|
| 3,060,084 | 10/1962 | Littler | 71/DIG. 1 |
| 3,689,507 | 9/1972 | Gates et al. | 71/88 |
| 3,896,151 | 7/1975 | Gates | 71/88 |
| 3,946,048 | 3/1976 | Fischer et al. | 71/88 |
| 3,948,636 | 4/1976 | Marks | 71/DIG. 1 |
| 4,071,617 | 1/1978 | Graves et al. | 71/DIG. 1 |

FOREIGN PATENT DOCUMENTS

| | | | |
|---|---|---|---|
| 851250 | 10/1960 | United Kingdom | 71/DIG. 1 |
| 1047601 | 11/1966 | United Kingdom | 71/DIG. 1 |
| 1063714 | 3/1967 | United Kingdom | 71/DIG. 1 |

OTHER PUBLICATIONS

McCutcheon, "Detergents & Emulsifiers", 1970, Ann. (1970), Allured Pub. Co., pp. 60, 74 & 176, 177 (1970).

*Primary Examiner*—Glennon H. Hollrah
*Attorney, Agent, or Firm*—Wenderoth, Lind & Ponack

[57] ABSTRACT

The invention provides herbicidal aqueous suspensions comprising from 0.05 to 700 g/l of a substituted benzofuran herbicide of the formula:

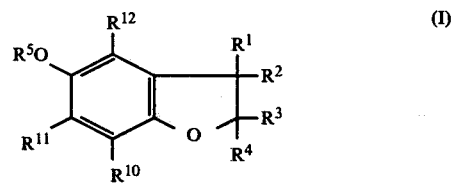

(where $R^1$, $R^2$, $R^3$, $R^4$, $R^5$, $R^{10}$, $R^{11}$ and $R^{12}$ are as defined in the specification), at least 85% by weight of the particles of said compound having a diameter less than 5 microns, from 0.5 to 50 g/l of a suspending agent (preferably a polycarboxylated vinyl polymer), and from 0.5 to 30%, based on the total content of compounds of formula I present, of a block copolymer of ethylene oxide and propylene oxide having a reversible thickening temperature as defined in the specification of 45° C. or above.

8 Claims, No Drawings

COMPOSITION

This is a continuation, of application Ser. No. 737,987, filed Nov. 2, 1976 now abandoned.

This invention relates to compositions.

We have invented new, particularly useful, formulations of certain known substituted benzofuran herbicides. Many of the said herbicides are described and claimed in our United Kingdom Pat. No. 1,271,659.

The substituted benzofuran herbicides which may be formulated in accordance with the invention are those of the formula:

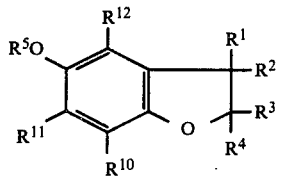

(I)

wherein $R^1$, $R^2$, and $R^3$ are the same or different and are hydrogen or alkyl (for example of 1-6 carbon atoms such as methyl or ethyl), or $R^1$ and $R^2$ together or $R^2$ and $R^3$ together form an alkylene chain (for example of 2-5 carbon atoms); $R^4$ is hydroxy, alkoxy (for example of 1-8 carbon atoms, especially 1-4 carbon atoms, such as methoxy, ethoxy or butoxy), substituted alkoxy (for example of 1-8 carbon atoms substituted by halogen or alkoxy such as chloroethoxy or methoxyethoxy), alkenyloxy (for example of 2-4 carbon atoms such as allyloxy), alkylthio (for example of 1-4 carbon atoms such as methylthio or ethylthio), substituted alkenyloxy (for example of 2-4 carbon atoms substituted by halogen such as chloroallyloxy), alkynyloxy (for example of 2-6 carbon atoms such as propargyloxy or butynyloxy), substituted alkynyloxy (for example of 2-4 carbon atoms substituted by halogen such as chlorobutynyloxy), aryloxy (for example phenoxy), substituted aryloxy (for example substituted by nitro or halogen such as nitrophenoxy), the group $NR^6R^7$ in which $R^6$ and $R^7$ are alkyl (for example of 1-4 carbon atoms such as methyl or ethyl) or substituted alkyl (for example of 1-4 carbon atoms substituted by halogen such as haloethyl) or together with the nitrogen atom form a heterocyclic ring, substituted or unsubstituted such as morpholine, pyrrolidine, piperidine or methyl piperazine, the group —$OCOR^{13}$, the group —$OSO_2R^{14}$ or the group —O—O—$R^{15}$, in which $R^{13}$ is alkyl (for example of 1-4 carbon atoms such as methyl or isopropyl), alkenyl (for example of 2-4 carbon atoms such as allyl), alkynyl (for example of 2-4 carbon atoms such as propargyl), substituted alkyl, alkenyl or alkynyl (for example aryloxy or halogen substituted such as trifluoromethyl, phenoxymethyl or chloroethyl), aryl (for example phenyl), substituted aryl (for example halogen or alkyl substituted such as chlorophenyl or tolyl), alkylamino (for example of 1-4 carbon atoms such as methylamino), dialkylamino (for example of 2-8 carbon atoms such as dimethylamino), alkoxy (for example of 1-6 carbon atoms such as methoxy or ethoxy), aryloxy (for example phenoxy), arylamino (for example phenylamino), substituted arylamino (for example substituted by halogen such as chlorophenylamino), substituted alkoxy (for example of 1-6 carbon atoms substituted by halogen or alkoxy such as methoxyethoxy), substituted aryloxy (for example halogen substituted such as chlorophenyl), alkenyloxy (for example of 2-4 carbon atoms such as allyloxy), substituted alkenyloxy (for example of 2-4 carbon atoms substituted by halogen such as chloroallyloxy), alkynyloxy (for example of 2-4 carbon atoms such as propargyloxy) or substituted alkynyloxy (for example of 2-4 carbon atoms substituted by halogen such as chlorobutynyloxy), in which $R^{14}$ is alkyl (for example of 1-4 carbon atoms such as methyl or ethyl), substituted alkyl (for example of 1-4 carbon atoms substituted by halogen such as chloroethyl), aryl (for example phenyl), substituted aryl (for example halogen, nitro or alkyl substituted such as chlorophenyl, nitrophenyl or tolyl), in which $R^{15}$ is alkyl (for example of 1-4 carbon atoms such as methyl, isopropyl or tertiary butyl), alkenyl (for example of 2-4 carbon atoms such as allyl) or alkynyl (for example of 2-4 carbon atoms such as propargyl); or $R^3$ and $R^4$ together represent an oxygen atom or the group $=NR^{16}$ in which $R^{16}$ is alkyl (for example of 1-4 carbon atoms such as methyl or isopropyl) or cycloalkyl (for example of 5 or 6 carbon atoms such as cyclohexyl); $R^5$ is the group $R^8CO$— or the group $R^9SO_2$— or the group $R^9SO$— or the group $R^{31}R^{32}NSO_2$—, in which $R^8$ is halogen substituted alkyl (for example of 1-4 carbon atoms such as chloromethyl, dichloroethyl, trichloroethyl or bromoethyl), $R^9$ is alkyl (for example of 1-4 carbon atoms such as methyl or ethyl), substituted alkyl (for example of 1-4 carbon atoms substituted by halogen or alkoxy such as chloromethyl, methoxypropyl and bromoethyl) aryl (for example phenyl) or substituted aryl (for example substituted halogen or alkyl such as chlorophenyl or tolyl), and $R^{31}$ and $R^{32}$ are the same or different and are hydrogen, alkyl (for example of 1-4 carbon atoms such as methyl or ethyl), substituted alkyl (for example of 1 to 4 carbon atoms, especially chloro-substituted, such as 2-chloroethyl), carboxylic acyl (for example of 1 to 4 carbon atoms, such as acetyl) or substituted carboxylic acyl (for example of 1 to 4 carbon atoms, especially chloro-substituted, such as chloroacetyl); and $R^{10}$, $R^{11}$ and $R^{12}$ are the same or different and are hydrogen, alkyl (for example of 1-4 carbon atoms such as methyl, ethyl or isopropyl), halogen (for example chlorine or bromine), cyano, acyl (for example of 2-6 carbon atoms such as acetyl) or alkoxy (for example of 1-4 carbon atoms such as methoxy), provided that said compound has a melting point of 50° C. or above, and a water solubility of at most 0.1% at 25° C.

The preferred compounds of formula I are those wherein $R^1$ and $R^2$ both represent methyl, $R^3$, $R^{10}$, $R^{11}$ and $R^{12}$ represent hydrogen, $R^4$ represents alkoxy (especially ethoxy, propoxy or isopropoxy), alkenyloxy (especially allyloxy), alkynloxy (especially propargyloxy), a group $NR^6R^7$ where $R^6$ and $R^7$ together with the nitrogen atom form an unsubstituted heterocyclic ring (especially morpholino or piperidino), a group —O-$COR^{13}$ where $R^{13}$ is alkyl (especially methyl), or, together with $R^3$, represents an oxygen atom, and $R^5$ represents a group $R^9SO_2$— where $R^9$ is alkyl (especially methyl) or a group $R^{31}R^{32}NSO_2$ where either one of $R^{31}$ and $R^{32}$ represents hydrogen, and the other represents alkyl (especially methyl), or one of $R^{31}$ and $R^{32}$ represents methyl and the other represents carboxylic acyl (especially acetyl) or substituted carboxylic acyl (especially chloroacetyl).

A specifically preferred compound which may be formulated in accordance with the present invention is 2-ethoxy-2,3-dihydro-3,3-dimethylbenzofuran-5-yl methanesulphonate (common name ethofumesate).

In one aspect, this invention provides a herbicidal aqueous suspension comprising water, one or more compounds of formula I as defined hereinbefore, a suspending agent, and a surface active agent which comprises a block copolymer of ethylene oxide and propylene oxide, and which has a reversible thickening temperature as defined hereinafter of 45° C. or above.

By the term 'reversible thickening temperature' as used herein is meant the temperature at which an observable marked change in viscosity occurs on heating a milled aqueous suspension comprising 48.5% w/v of pure ethofumesate, 1.5% w/v of the surface active agent, 4.85% w/v of Dyapol PFS (a sodium salt anionic sulphonated condensation product deflocculating agent by Yorkshire Chemicals Limited) and 0.1% w/v of Antifoam RD (silicone-based antifoam agent by Dow Corning).

The invention provides also a method of combating weeds at a locus infested or liable to be infested with them, which method comprises applying to the locus a weed-combating amount of a suspension of the present invention.

The suspensions can be prepared by a process comprising admixing the ingredients. The particles of the active ingredient(s) in the suspensions are preferably less than 5 microns diameter, desirably at least 85% by weight of the particles being below this limit. Particle sizes in this specification are as measured on a Coulter Counter. Conveniently, the active ingredient(s) of greater particle size than is desired in the suspension are admixed with other ingredients (including the block copolymer of ethylene oxide and propylene oxide) and comminuted to this size e.g. in a ball mill. The suspending agent may conveniently be admixed as a solution or suspension thereof in water.

The present suspensions preferably contain in toto from 0.05 to 700 g/l and more preferably from 0.05 to 600 g/l of the active ingredient(s).

Usually the suspension is initially produced in the form of a concentrate, preferably containing from 100 to 700 g/l and more preferably from 100 to 600 g/l and especially at least 300 g/l, for example 500 g/l, in toto of the active ingredient(s).

The concentrate is then usually diluted with water for application, usually such that the concentration of the active ingredient(s) applied is from 0.05 to 5 g/l, and more preferably from 0.5 to 5 g/l. However, greater concentrations may be applied if desired, especially if low-volume application is preferred.

The suspensions generally contain from 0.5 to 50 g/l, preferably from 0.5 to 35 g/l, of the suspending agent. More preferably, the suspending agent is present in an amount of from 0.5 to 10 g/l.

The suspending agent is very preferably a polycarboxylated vinyl polymer, and is most preferably such a polymer wherein some or all of the carboxyl groups are in the form of alkali-metal, ammonium or amine salts. These polymers have neutralisation equivalents ranging from 71 to 800 (expressed as grams of dry polymer neutralised by one equivalent of sodium or potassium hydroxide). 1% aqueous solutions of these polymers generally have Brookfield viscosities (20 rpm) of less than 7000 cps, though, upon neutralisation of such solutions to a pH of 7, the viscosities increase to between 10,000 and 70,000 cps. Examples of such polymers are carboxyvinyl polymers (e.g. those available under the trade mark Carbopol, from the Goodrich Chemical Company, especially Carbopol 941) or acrylic copolymers containing carboxyl groups (e.g. those available under the trade mark Viscalex, from the Allied Colloids Company, especially Viscalex HV 30).

Other preferred suspending agents are the high molecular weight polysaccharide gums obtained by fermenting sugars derived from starch. These gums generally have molecular weights of about 2,000,000 to 50,000,000, contain reactive hydroxyl and carboxyl groups, are slightly hygroscopic, dissolve easily and completely in cold water to produce high viscosity colloidal solutions, and swell rapidly in hydrated aqueous solutions to yield essentially neutral, non-thixotropic stable solutions.

Preferably the polysaccharide gum is a Xanthomonas hydrophilic colloid (otherwise known as a xanthan gum), e.g. that available under the trade mark Kelzan from Kelco Company. A Xanthomonas hydrophilic colloid is one produced by fermentation by a bacterium of the genus Xanthomonas, e.g. *Xanthomonas campestris*.

The block copolymer of ethylene oxide and propylene oxide employed as the surface active agent is preferably derived from the addition of ethylene oxide to a polyoxypropylene chain to form a polyol. More preferred are those polyols with a polyoxypropylene chain of molecular weight greater than 1,500, and especially greater than 1,800. More desirably, the polyol contains from 30 to 70%, e.g. from 40 to 60%, e.g. about 50% by weight of ethylene oxide. Preferred such polyols are those available under the trade name 'Pluronic' from Ugine Kuhlmann, especially those having the code numbers F68, F127, L62, L103, P75, P94, P104 and P105.

The suitability of a particular block copolymer of ethylene oxide and propylene oxide may be readily determined by a person skilled in pesticide formulation by employing the techniques described hereinbefore for ascertaining its reversible thickening temperature.

The block copolymer of ethylene oxide and propylene oxide is preferably present in an amount by weight of from 0.5 to 30%, and more preferably from 3 to 15% of the content of the compound(s) of formula I.

A deflocculating agent is desirably present in the suspensions of the invention, and is preferably a sodium salt anionic sulphonated condensation product, e.g. that available from Yorkshire Chemicals Limited under the trade name 'Dyapol PFS.'

The deflocculating agent is preferably present in an amount of from 0.5 to 30% by weight, and more especially from 3 to 15% by weight based upon the weight of the compound(s) of formula I present.

The suspensions may contain compatible additional, water-miscible, materials as carriers though preferably the water is the sole carrier.

The suspensions may contain additives such as antifoam agents (e.g. a silicone based antifoam agent) for example in amount 0.02-2% by weight of the continuous phase, antifreeze agents (e.g. ethylene glycol) for example in amount 5-20% by weight of the continuous phase, or preservatives (e.g. formaldehyde), for example in an amount of 0.02-2% by weight of the continuous phase.

Other compatible pesticides, e.g. herbicides, insecticides, fungicides, or plant growth regulants may be included in the concentrate suspensions or the diluted formulations. It is particularly useful to include one or more herbicides, especially herbicides useful for the selective control of weeds in sugar beet. Examples of such herbicides, which may be employed where appropriate, in the form of functional derivatives, e.g. metal salts, include phenoxyaliphatic acids (e.g. 2,4-D, i.e. 2,4-dichlorophenoxyacetic acid; MCPA, i.e. 4-chloro-2-methyl-phenoxyacetic acid; 2,4,5-T, i.e. 2,4,5-trichlorophenoxy-acetic acid; 2,4-DB, i.e. 4-(2,4-dichlorophenoxy)butyric acid; MCPB, i.e. 4-(4-chloro-2-methylphenoxy)butyric acid; and CMPP, i.e. 2-(4-chloro-2-methylphenoxy)-propionic acid); substituted ureas (e.g. monuron, i.e. 3-(4-chlorophenyl)-1,1-dimethylurea; diuron, i.e. 3-(3,4-dichlorophenyl)-1,1-dimethylurea; neburon, i.e. 1-butyl-3-(3,4-dichlorophenyl)-1-methylurea; monolinuron, i.e. 3-(4-chloro-phenyl-1-methoxy-1-methylurea; linuron, i.e. 3-(3,4-dichlorophenyl)-1-methoxy-1-methylurea; fenuron, i.e. 1,1-dimethyl-3-phenylurea; and benzthiazuron, i.e. 1-(benzothiazol-2-yl)-3-methylurea); triazines (e.g. simazine, i.e. 2-chloro-4,6-di(ethylamino)-1,3,5-triazine; atrazine, i.e. 2-chloro-4-ethylamino-6-isopropylamino-1,3,5-triazine; trietazine, i.e. 2-chloro-4-diethylamino-6-ethylamino-1,3,5-triazine; and prometryne, i.e. 2,4-di(isopropylamino)-6-methylthio-1,3,5-triazine); DNOC, i.e. 4,6-dinitro-o-cresol; PCP, i.e. pentachlorophenol; ioxynil, i.e. 4-hydroxy-3,5-diiodobenzonitrile; bromoxynil, i.e. 3,5-dibromo-4-hydroxybenzonitrile; dichlobenil, i.e. 2,6-dichlorobenzonitrile; diquat, i.e. 1,1'-ethylene-2,2'-bipyridylium ion; paraquat, i.e. 1,1'-dimethyl-4,4'-bipyridylium ion; 2,3,6-trichlorobenzoic acid; dalapon, i.e. 2,2-dichloropropanoic acid; dicamba, i.e. 3,6-dichloro-2-methoxybenzoic acid; TCA, i.e. trichloroacetic acid; chloropropham, i.e. isopropyl 3-chlorophenylcarbamate; barban, i.e. 4-chloro-but-2-ynyl-3-chlorophenylcarbamate; EPTC, i.e. S-ethyl dipropyl-thiocarbamate; butylate, i.e. S-ethyl di-isobutylthiocarbamate; diallate, i.e. S-2,3-dichloroallyl di-isopropylthiocarbamate; allidochlor, i.e. N,N-diallylchloroacetamide; propachlor, i.e. 2-chloro-N-isopropyl-N-phenylacetamide; bromacil, i.e. 5-bromo-3-sec-butyl-6-methyluracil; lenacil, i.e. 3-cyclohexyl-6,7-dihydro-1H-cyclopentapyrimidine-2,4-dione; maleic hydrazide; salts of methanearsonic acid; cacodylic acid; aminotriazole, i.e. 3-amino-1,2,4-triazole; picloram, i.e. 4-amino-3,5,6-trichloropicolinic acid; trifluralin, i.e. 2,6-dinitro-N,N-dipropyl-4-trifluoromethylaniline; S,S,S-tributyl phosphorotrithioate; phenmedipham, i.e. 3-m-tolylcarbamoyloxy phenylcarbamate; azolamid, i.e. N-isobutyl-2-oxoimidazolidine-1-carboxamide; triallate, i.e. S-2,3,3-trichloroallyl di-isopropylthiocarbamate; cycloate, i.e. S-ethyl cyclohexylethylthiocarbamate; carbetamide, i.e. 1-(ethyl-carbamoyl)ethylphenylcarbamate; diphenamid, i.e. N,N-dimethyldiphenylacetamide; pebulate, i.e. S-propyl butylethylthiocarbamate; benfluralin, i.e. N-butyl-N-ethyl-2,6-dinitro-4-trifluoromethylaniline; metobromuron, i.e. 3-(4-bromophenyl)-1-methoxy-1-methylurea; pyrazon, i.e. 5-amino-4-chloro-2-phenyl-pyridazin-3-one; N-(phosphonomethyl)glycine; 3-(methoxycarbonylamino)phenyl N-(3,5-dimethylphenyl)-carbamate; and 3-ethoxycarbonylaminophenyl N-phenylcarbamate. Especially preferred are phenmedipham, pyrazon, lenacil and cycloate.

The compositions of the invention may alternatively be applied in sequence with one or more of the herbicides listed above.

The ratio of the total amount of the compound(s) of formula I present to the or each further herbicide present is preferably from 1:5 to 5:1 by weight.

The or each additional herbicide may be incorporated in the suspension of the present invention either before dilution of a concentrate if it does not upset the stability of the concentrate unacceptably, or after.

The suspensions are of excellent stability and the concentrates retain their homogeneous and flowable nature very well during storage even at fluctuating temperatures. Moreover, they possess excellent dispersability in the medium used to dilute them for application. The suspensions are particularly useful for the control of weeds in crops, e.g. sugar beet, sunflower, tobacco, pastures and cruciferous crops, and especially sugar beet.

The rate of application is usually 0.5–8 kg in toto of the compound(s) of formula I per hectare, for example 1–4 kg per hectare.

The suspensions may be applied pre- or post-planting of the crop. They may be employed for post-emergence or, more preferably, pre-emergence use.

The invention is illustrated by the following Examples.

EXAMPLE 1

An aqueous flowable suspension concentrate was prepared from the following as described below:

| | |
|---|---|
| Ethofumesate technical, 98% purity | 510g |
| Pluronic P75 (block copolymer produced by condensation of ethylene oxide with polyoxypropylene chain of molecular weight about 2050, wherein the polyoxyethylene constitutes 50% by weight of the block copolymer); by Ugine-Kuhlmann Company | 15g |
| Polyfon H (sodium salt of sulphonated Kraft Lignin by Westvaco Corporation) | 15g |
| Antifoam RD emulsion (silicone based antifoam emulsion by Dow Corning Corporation) | 0.5g |
| Ethylene glycol | 80g |
| Xanthan gum (Kelzan by Kelco Company) | 2g |
| Formaldehyde | 1g |
| Water to 1 litre | approx 510 ml |

Water (360 ml), the Antifoam RD emulsion, the Pluronic P75, the Polyfon H, the ethylene glycol and the ethofumesate were in order charged to a stirred ball mill. The mixture was milled until greater than 95% by weight of the ethofumesate had a particle size below 5 microns as determined by Coulter Counter measurement. A solution of the Xanthan gum and the formaldehyde (a preservative for the Xanthan gum) in water (150 ml) was then incorporated into the milled product using a paddle stirrer until homogeneity was obtained. The pH of the suspension was then adjusted to 7.0 with 10% aqueous hydrochloric acid.

EXAMPLE 2

By a process similar to that described above in Example 1, a flowable herbicidal concentrate was prepared of identical constitution except that 2.5 g of Carbopol 941 (by the Goodrich Chemical Company) replaced the Xanthan gum and the formaldehyde. The water, Antifoam RD emulsion, Pluronic P75, Polyfon H, ethylene glycol and ethofumesate were made into a suspension as described above in Example 1. The pH of this suspension was adjusted to 7.0 by the addition of 10% aqueous hydrochloric acid, and a solution of the Carbopol 941 acid was dispersed homogeneously therein. The pH of the suspension was then adjusted to 7.0 by the addition of 10% aqueous sodium hydroxide.

EXAMPLE 3

By a process similar to that described above in Example 1, a flowable herbicidal concentrate was prepared of identical constitution except that 32 g of Viscalex HV30 (by the Allied Colloids Manufacturing Company) related the Xanthan gum and the formaldehyde. The pH of the suspension was then adjusted to 8.0 by the addition of 10% aqueous hydrochloric acid.

EXAMPLE 4

For comparison, suspension concentrates identical to those of Examples 1, 2 and 3 were prepared, except that the suspending agent in each case (respectively the Xanthan gum, the Carbopol 941 and the Viscalex HV30) was omitted.

EXAMPLE 5

Also for comparison, suspension concentrates identical to those of Examples 1 to 3 were produced, except that 15 g of a codensate of lauryl alcohol with 6 moles of ethylene oxide (Serfal LA60 by D G Bennet Chemicals Limited) replaced the Pluronic P75.

EXAMPLE 6

The suspension concentrates of Examples 1, 2 and 3 were compared in a temperature storage test (the temperatures in one test being maintained at 40° C. and in another being maintained successively for periods of 12 hours at 12° C. and 38° C. over a period of 6 months) with the suspension concentrates of Examples 4 and 5. At the end of the storage period, it was found that the suspensions of Examples 1, 2 and 3 had no hard sediment and were still flowable, but those of Example 4 had settled to leave a hard sediment and about 50% by volume of clear supernatant liquid. Moreover, it was found that the sediment could not be redispersed in the supernatant liquid by methods which a user could reasonably be expected to use, including stirring and shaking.

The suspensions of Example 5 at the end of the storage tests were found no longer to be flowable, and moreover could not be rendered usable by any method which a user might reasonably be expected to use, including stirring and shaking.

EXAMPLE 7

Aqueous flowable suspension concentrates are prepared identical to those of Examples 1, 2 and 3 except that the ethofumesate technical is replaced by appropriate amounts of the following compounds (which represent a preferred group of compounds for the compositions of the invention) to give a concentration of pure compound of 500 g per liter:

2-ethoxy-2,3-dihydro-3,3-dimethylbenzofuran-5-yl ethanesulphonate;
2-morpholino-2,3-dihydro-3,3-dimethylbenzofuran-5-yl methanesulphonate;
2-piperidino-2,3-dihydro-3,3-dimethylbenzofuran-5-yl methanesulphonate;
2-oxo-2,3-dihydro-3,3-dimethylbenzofuran-5-yl methanesulphonate;
2-acetyloxy-2,3-dihydro-3,3-dimethylbenzofuran-5-yl methanesulphonate;
2-ethoxy-2,3-dihydro-3,3-dimethylbenzofuran-5-yl methylaminosulphonate;
2-ethoxy-2,3-dihydro-3,3-dimethylbenzofuran-5-yl dimehylaminosulphonate;
2-ethoxy-2,3-dihydro-3,3-dimethylbenzofuran-5-yl N-methyl-N-acetylaminosulphonate;
2-ethoxy-2,3-dihydro-3,3-dimethylbenzofuran-5-yl N-methyl-N-chloroacetylaminosulphonate;
2-propoxy-2,3-dihydro-3,3-dimethylbenzofuran-5-yl methylaminosulphonate;
2-propoxy-2,3-dihydro-3,3-dimethylbenzofuran-5-yl dimethylaminosulphonate;
2-isopropoxy-2,3-dihydro-3,3-dimethylbenzofuran-5-yl methylaminosulphonate;
2-isopropoxy-2,3-dihydro-3,3-dimethylbenzofuran-5-yl dimethylaminosulphonate;
2-allyloxy-2,3-dihydro-3,3-dimethylbenzofuran-5-yl methylaminosulphonate;
2-allyloxy-2,3-dihydro-3,3-dimethylbenzofuran-5-yl dimethylaminosulphonate;
2-propargyloxy-2,3-dihydro-3,3-dimethylbenzofuran-5-yl methylaminosulphonate;
2-propargyloxy-2,3-dihydro-3,3-dimethylbenzofuran-5-yl dimethylaminosulphonate;
2-morpholino-2,3-dihydro-3,3-dimethylbenzofuran-5-yl methylaminosulphonate;
2-morpholino-2,3-dihydro-3,3-dimethylbenzofuran-5-yl dimethylaminosulphonate.

On storage as set out in Example 6, all suspensions remain flowable and have no hard sediment or clear supernatant liquid.

EXAMPLE 8

Determination of Reversible Thickening Temperature

A mixture of milled technical ethofumesate (98% pure; 1020 g), Dyapol PFS (deflocculating agent from Yorkshire Chemicals Limited; 100 g) Antifoam RD (antifoam agent from Dow Corning; 2 g) and water (844 ml) was milled for 5½ hours, giving a suspension of milky consistency with a specific gravity of 1.12. A portion of this suspension (8.5 ml) was then admixed with 1.5 ml of a 10% aqueous solution of Pluronic F68 (surface active agent by Ugine Kuhlmann). This mixture was then heated slowly on a water bath whilst monitoring its temperature. At 51° C. a significant thickening of the suspension occurred which was readily observable by the experimentor. The suspension remained in this condition on further heating, but reverted on cooling to below 51° C. to its former consistency. The reversible thickening temperature of Pluronic F68 was therefore assessed as 51° C.

Many other surface active agents were evaluated in this manner, selected results being as follows:

| | |
|---|---|
| Pluronic P75 | >62° C. |
| Pluronic F127 | >62° C. |
| Pluronic P105 | >62° C. |
| Pluronic P94 | >62° C. |
| Pluronic L103 | >62° C. |
| Pluronic L62 | 49° C. |

We claim:

1. An aqueous suspension concentrate which comprises from 100 to 700 g/l of 2-ethoxy-2,3,dihydro-3,3-dimethylbenzofuran-5-yl methane sulphonate at least 85% by weight of the particles thereof having a diameter of less than 5 microns as measured by Coulter Counter, from 0.5 to 10 g/l of a xanthomonas hydrophilic colloid, from 0.5 to 30% by weight, based upon the weight of said sulphonate present, of a surface active agent which comprises a block copolymer of ethylene oxide and propylene oxide and which has a reversible thickening temperature of 45° C. or above, and from 0.5 to 30% by weight, based upon the weight of said sulphonate present, of an anionic deflocculating agent.

2. A suspension concentrate according to claim 1, which comprises from 100 to 600 g/l of 2-ethoxy-2,3,dihydro-3,3-dimethylbenzofuran-5-yl methane sulphonate.

3. A suspension concentrate according to claim 1, wherein the block copolymer of ethylene oxide and propylene oxide is a polyol derived from the addition of ethylene oxide to a polyoxypropylene chain.

4. A suspension concentrate according to claim 3, wherein the polyoxypropylene chain has a molecular weight greater than 1500.

5. A suspension concentrate according to claim 3, wherein the polyol contains from 30 to 70% by weight of ethylene oxide.

6. A suspension concentrate according to claim 1, wherein the block copolymer of ethylene oxide and propylene oxide is present in an amount of from 3 to 15% by weight based upon the weight of the sulphonate which is present.

7. A suspension concentrate according to claim 1, wherein the anionic deflocculating agent is present in an amount of from 3 to 15% by weight, based upon the weight of said sulphonate present.

8. An aqueous suspension concentrate according to claim 1, which comprises from 100 to 600 g/l of 2-ethoxy-2,3-dihydro-3,3-dimethylbenzofuran-5-yl methane sulphonate, from 0.5 to 10 g/l of a xanthomonas hydrophilic colloid, from 3 to 15% by weight based upon the weight of said sulphonate present of a polyol derived from the addition of ethylene oxide to a polyoxypropylene chain having a molecular weight greater than 1500, the polyol containing from 30 to 70% by weight of ethylene oxide, and from 3 to 15% by weight based upon the weight of said sulphonate present of a sodium salt anionic deflocculating agent.

* * * * *